United States Patent [19]

Pringle et al.

[11] Patent Number: 5,260,482
[45] Date of Patent: Nov. 9, 1993

[54] ENANTIOMERIC RESOLUTION

[75] Inventors: Patricia Pringle, Pinewood; William T. Murray, Orangeburg; Douglas K. Thompson, Orangeburg; Azfar A. Choudhury, Orangeburg; Deepak R. Patil, Orangeburg, all of S.C.

[73] Assignee: Ethyl Corporation, Richmond, Va.

[21] Appl. No.: 960,990

[22] Filed: Oct. 14, 1992

[51] Int. Cl.⁵ .............................. C07B 57/00
[52] U.S. Cl. .................... 562/401; 558/414; 560/56; 560/57; 560/60; 560/100; 560/101; 560/105
[58] Field of Search .......... 562/401; 558/414; 560/56, 57, 60, 100, 101, 105

[56] References Cited

U.S. PATENT DOCUMENTS

| | | | |
|---|---|---|---|
| 4,831,147 | 5/1989 | Russell | 546/302 |
| 4,865,770 | 9/1989 | Piselli | 562/402 |
| 4,910,309 | 3/1990 | Kershner et al. | 544/354 |
| 4,931,587 | 6/1990 | Piselli | 562/401 |
| 4,973,745 | 11/1990 | Blaschke et al. | 562/401 |

OTHER PUBLICATIONS

Collet et al., Chem. Rev. 80(3), pp. 215-230 (1980).
Jaques et al., *Enantiomers, Racemates and Resolutions*, Chapter 3, J. Wiley & Sons, New York, N.Y., (1981), pp. 167-213.
Collet, A., pp. 91-110, *Problems and Wonders of Chiral Molecules*, Simonyi, M. (Ed.), Akademiai Keado, Budapest (1990).

*Primary Examiner*—José G. Dees
*Assistant Examiner*—Vera C. Clarke
*Attorney, Agent, or Firm*—Richard J. Hammond

[57] ABSTRACT

A process for obtaining a substantially pure enantiomer of an aryl-substituted aliphatic carboxylic acid is described. The process combines an aryl substituted aliphatic carboxylic acid, a base and water in an inert solvent to make a hydrated salt of the said acid. The process leads to enhanced yield of an enantiomerically enriched hydrated salt of the carboxylic acid.

19 Claims, No Drawings

ENANTIOMERIC RESOLUTION

FIELD OF INVENTION

This invention relates to a process for obtaining highly pure enantiomers of aryl-substituted carboxylic acids from a mixture of enantiomers.

BACKGROUND OF INVENTION

The resolution of racemates constitutes the main method for industrial preparation of pure enantiomers. Methods for such resolution include: direct preferential crystallization; crystallization of the diastereomeric salts and kinetic resolution. Pure enantiomers may also be produced by asymmetric synthesis (reaction of a chiral reagent or catalyst with a prochiral substrate).

Also referred to as resolution by entrainment, preferential crystallization is widely used on an industrial scale; for example, in the manufacture of α-methyl-L-dopa and chloramphenicol. It is technically feasible only with racemates which are so-called conglomerates. Unfortunately, less than 20 percent of all racemates are conglomerates. The rest are racemic compounds which cannot be separated by preferential crystallization.

If the racemate is not a conglomerate, a homogeneous solid phase of the two enantiomers co-exists in the same unit cell. These materials may be separated via diastereomer crystallization, which generally involves reaction of the racemate with an optically pure acid or base (the resolving agent) to form a mixture of diastereomeric salts which are then separated by crystallization. Ibuprofen, for example, is such a compound.

Diastereomer crystallization is widely used for the industrial synthesis of pure enantiomers. A typical example is the Andeno process for the manufacture of (D)-(−)-phenylglycine, an antibiotic intermediate, using optically pure camphor sulfonic acid as the resolving agent. Also see U.S. Pat. No. 4,752,417 for a diastereomeric procedure for resolving certain phenylacetic acid derivatives and U.S. Pat. No. 4,973,745 for resolving 2-arylpropionic acids.

The theoretical once-through yield of a resolution via diastereomer crystallization is 50 percent. However, in practice, a single recrystallization produces a composition that is simply enantiomerically enriched.

Another method for the resolution of racemates is kinetic resolution, the success of which depends on the fact that the two enantiomers react at different rates with a chiral addend.

Kinetic resolution can also be effected using chiral metal complexes as chemocatalysts, e.g., the enantioselective rhodium-BINAP-catalyzed isomerization of chiral allylic alcohols to the analogous prostaglandin intermediates reported by Noyori.

The enantioselective conversion of a prochiral substrate to an optically active product, by reaction with a chiral addend, is referred to as an asymmetric synthesis. From an economic viewpoint, the chiral addend functions in catalytic quantities. This may involve a simple chemocatalyst or a biocatalyst. An example of the former is the well-known Monsanto process for the manufacture of L-dopa by catalytic asymmetric hydrogenation. See Knowles, et al., J. Am. Chem. Soc., 97, 2567 (1975). An example of the latter is the Genex process for the synthesis of L-phenylalanine by the addition of ammonia to transcinnamic acid in the presence of L-phenylalanine ammonia lyase (PAL). See Hamilton et al., Trends in Biotechnology, 3, 64–68, (1985). Also see Jacques et al., Enantiomers, Racemates and Resolutions, Chapter 3 (1981) incorporated herein by reference.

With the exception of the preferential crystallization process when applied to true conglomerates, the prior art processes typically produce a first mixture that is enantiomerically enriched. A number of crystallizations are required to obtain a substantially pure enantiomer.

OBJECTS OF THE INVENTION

It is an object of the present invention to provide a process for obtaining a substantially pure enantiomer of an arylsubstituted aliphatic carboxylic acid or the ester thereof.

It is a further object of the present invention to obtain such a substantially pure enantiomer from a composition of enantiomerically enriched or racemic aryl-substituted aliphatic carboxylic acid or the ester thereof.

PREFERRED EMBODIMENTS OF THE INVENTION

In the present specification, alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl;

cycloalkyl means cyclic alkyl having 3 to 7 carbon atoms and includes cyclopropyl, cyclobutyl, cyclopentyl, cyclohexyl and cycloheptyl;

substituted phenyl or substituted naphthyl means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or branched alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl;

haloalkyl means straight or branched chain alkyl having 1 to 10 carbon atoms which is substituted at least one halogen as mentioned above;

hydroxyalkyl means that the alkyl moiety is straight or branched chain alkyl having 1 to 8 carbon atoms, and includes, for example, hydroxymethyl, 2-hydroxyethyl, 3-hydroxypropyl, 4-hydroxybutyl, 6-hydroxyhexyl, 8-hydroxyoctyl, 1-hydroxyethyl, 1- hydroxy-2-propyl, 2-hydroxypropyl, 2,3-dihydroxypropyl, 1,3-dihydroxy-2-propyl;

alkoxyalkyl means that the alkoxy moiety and the alkyl moiety each are straight or branched chain ones having 1 to 8 carbon atoms, and includes, for example, methoxymethyl, ethoxymethyl, propoxymethyl, isopropoxymethyl, butoxymethyl, isobutoxymethyl, tertiary butoxymethyl, pentyloxymethyl, hexyloxymethyl, heptyloxymethyl, octyloxymethyl, 2-methoxyethyl, 2-ethoxyethyl, 2-propoxyethyl, 2-butoxyethyl, 2-hexyloxyethyl, 2-octyloxyethyl, 3-methoxypropyl, 3-ethoxypropyl, 3-propoxypropyl, 3-butoxypropyl, 3-hexyloxypropyl, 3-octyloxypropyl, 4-methoxybutyl, 4-ethoxybutyl, 4-propoxybutyl, 4-butoxybutyl, 4-hexyloxybutyl, 4-octyloxybutyl, 5-methoxypentyl, 5-ethoxypentyl, 5-propoxypentyl, 5-butoxypentyl, 5-pentyloxypentyl, 5-hexyloxypentyl, 5-octyloxypentyl, 6-methoxyhexyl, 6-ethoxyhexyl, 6-propoxyhexyl, 6-butoxyhexyl, 6-pentyloxyhexyl, 6-hexyloxyhexyl, 6-oxtyloxyhexyl, 8-methoxyoctyl, 8-ethoxyoctyl, 8-butoxyoctyl, 8-hexyloxyoctyl and 8-octyloxyoctyl;

acyloxyalkyl means that the acyl moiety is alkanoyl having 2 to 18 carbon atoms, benzoyl, substituted benzoyl, heteroarylcarbonyl or substituted heteroarylcarbonyl and the alkyl moiety is straight or branched chain alkyl having 1 to 8 carbon atoms, and includes, for example, acetoxymethyl, 2-acetoxyethyl, 3-acetoxypropyl, 4-acetoxybutyl, 6-acetoxyhexyl, 8-acetoxyoctyl, propionyloxymethyl, 2-propionyloxyethyl, 3-propionyloxypropyl, 4-propionyloxybutyl, 6-propionyloxyhexyl, 8- propionyloxyoctyl, isobutyryloxymethyl, 2-isobutyryloxyethyl, 4- isobutyryloxybutyl, pivaloyloxymethyl, 2-pivaloyloxyethyl, 4-pivaloyloxybutyl, butyryloxymethyl, 2-butyryloxyethyl, 4-butyryloxybutyl, valeryloxymethyl, 2-valeryloxyethyl, 4-valeryloxybutyl, hexanoyloxymethyl, 2-hexanoyloxyethyl, 4-hexanoyloxybutyl, octanoyloxymethyl, 2-octanoyloxyethyl, 4-octanoyloxybutyl, lauroyloxymethyl, 2-lauroyloxyethyl, 4-lauroyloxybutyl, stearoyloxymethyl, 2-stearoyloxyethyl, 4-stearoyloxybutyl, benzoyloxymethyl, 2-benzoyloxyethyl, 4-benzoyloxybutyl, furoyloxymethyl, 2-furoyloxyethyl, 4-furoyloxybutyl, thenoyloxymethyl, 2-thenoyloxyethyl, 4-thenoyloxybutyl, nicotinoyloxymethyl, 2-nicotinoyloxyethyl and 4-nicotinoyloxybutyl;

carboxyalkyl means that the alkyl moiety is straight or branched chain alkyl having 1 to 8 carbon atoms and includes, for example, carboxymethyl, 2-carboxymethyl, 3-carboxypropyl, 4- carboxybutyl, 6-carboxyhexyl and 8-carboxyoctyl;

alkoxycarbonylalkyl means that the alkoxy moiety and the alkyl moiety each are straight or branched chain ones having 1 to 8 carbon atoms, and includes, for example, methoxycarbonylmethyl, ethoxycarbonylmethyl, propoxycarbonylmethyl, isopropoxycarbonylmethyl, butoxycarbonylmethyl, isobutoxycarbonylmethyl, tertiary butoxycarbonylmethyl, pentlyoxycarbonylmethyl, hexyloxycarbonylmethyl, octyloxycarbonylmethyl, 2-methoxycarbonylethyl, 2-ethoxycarbonylethyl, 2-propoxycarbonylethyl, 2-butoxycarbonylethyl, 3-methoxycarbonylpropyl, 3-ethoxycarbonylpropyl, 3-propoxycarbonylpropyl, 3-butoxycarbonylpropyl, 4-methoxycarbonylbutyl, 4-ethoxycarbonylbutyl, 4-propoxycarbonylbutyl, 4-butoxycarbonylbutyl, 6-methoxycarbonylhexyl, 6-ethoxycarbonylhexyl, 8-methoxycarbonyloctyl and 8-ethoxycarbonyloctyl;

cyanoalkyl means that the alkyl moiety is straight or branched chain alkyl having 1 to 8 carbon atoms and includes, for example, cyanomethyl, 2-cyanoethyl, 3-cyanopropyl, 4-cyanobutyl, 6-cyanohexyl and 8-cyanooctyl; and The objective of the present invention is achieved by dissolving an enantiomerically enriched or racemic mixture of an aryl-substituted aliphatic carboxylic acid or the ester thereof in an inert solvent or a mixture of inert solvents. These materials have the following formula:

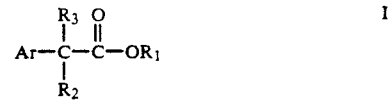

where $R_1$ is hydrogen or $C_1$ to $C_6$ linear or branched alkyl, $R_2$, and $R_3$ are hydrogen, alkyl, cycloalkyl, phenyl, substituted phenyl, naphthyl, substituted naphthyl, haloalkyl, hydroxyalkyl, alkoxyalkyl, acyloxyalkyl, carboxyalkyl, alkoxycarbonylalkyl or cyanoalkyl.

Ar is phenyl, substituted phenyl, naphthyl or substituted naphthyl.

Preferred compounds of Formula I are those of the formula:

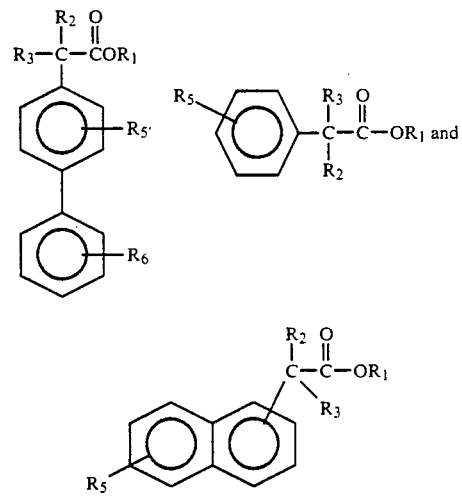

where $R_1$, and $R_2$ and $R_3$ are as previously defined and $R_5$ and $R_6$ are $C_1$ to $C_4$ linear or branched alkyl, $C_1$ to $C_4$ linear or branched alkoxy or halo.

The process of the present invention is particularly applicable to 2-(4-isobutylphenyl)propionic acid and especially in obtaining a preponderance of the d(+)isomer.

The invention is carried out by using a mixture of both the (+) and (−) (or dextro and levo rotatory forms) enantiomers of the carboxylic acids of formula I. However, it should be understood that the process itself does not convert one form of the stereoisomers to the other form but only separates such forms. Further in the preferred embodiment of this invention, the separation of enantiomers gives rise to a soluble product and an insoluble product which is enriched in one of the enantiomers. As such, a high purity product is obtained that requires a minimum number of recrystallizations (usually not more than two) to give a product with exceptionally high optical purity.

The process for the separation of the enantiomers used in the present invention is to first form a salt of the aliphatic carboxylic acid of formula I with an inorganic base. It is preferred that the inorganic base is a metal or a metallic or ammonium hydroxide, carbonate, bicarbonate or chloride. The metal may be any metal. Metals in Group I or II of the Periodic Table of Elements are preferred. Most preferably, the metal of the inorganic base is from Group IA. Especially preferred is sodium hydroxide.

An inert solvent can be added. The solvent should dissolve both the base and the aryl-substituted carboxylic acid or ester thereof and be inert to the starting materials and the products. Conveniently, with the proper selection of solvents, a solid crystalline material will precipitate from the reaction solution.

Any solvent that is not reactive with these carboxylic acids or esters is acceptable. Thus, various aliphatic hydrocarbon solvents, i.e., hexane, heptane, octane, etc., aromatic hydrocarbon solvents, i.e., benzene, toluene, xylene, and alcohol solvents, i.e., methanol, ethanol, i-propyl alcohol, etc., are preferred for such solvent. Particularly preferred are the aliphatic hydrocarbon solvents, especially hexane. It should be understood that mixtures of such solvents are also encompassed within the meaning of "inert solvent".

At this point in the reaction (after the admixture of the solvent with the base and the enriched aryl-substituted aliphatic carboxylic acid or ester thereof), the salt and solvent may be heated, e.g. to a temperature of about 0° C. to about 125° C., preferably about 40° C. to 60° C., or the heating can occur before the salt solution is formed. Heating is typically carried out from about 1 to about 16 hours, preferably from about 2 to about 8 hours.

It has been discovered that, in order to successfully precipitate one of the enantiomeric salts of the carboxylic acids of formula I from the reaction solution, sufficient amounts of separation-enhancing water must be present, i.e., the water enhances the formation and precipitation of the crystalline solid substantially pure enantiomer. Although the reaction of the enriched mixture with an inorganic base produces water as a product of the neutralization reaction, an additional amount of water is necessary to achieve an improved recovery of one of the enantiomers in the process of the present invention. The amount of base used to produce the enriched salt solution is from about 0.05 to about 0.95 mole, preferably from about 0.40 to about 0.80 moles, most preferably from about 0.45 to about 0.65 mole per mole of aryl substituted carboxylic acid. The amount of water that must be added to the inorganic base and carboxylic acid mixture to improve the recovery of one of the enantiomers is 0.05 to 2.00 moles, preferably from 0.1 to 2.5 moles, most preferably from 1 to 2 moles per mole of carboxylic acid.

The material recovered is the crystalline hydrated salt of the aryl-substituted aliphatic carboxylic acid. For example, if sodium hydroxide is used as the base in reacting with a carboxylic acid such as 2-(4-isobutylphenyl)propionic acid, the crystalline product obtained after addition of the inert solvent . is 2-(4-isobutylphenyl)propionic acid, sodium salt, dihydrate The process of the present invention will not produce the precipitated dihydrate in any significant yield, i.e., greater than 30% of theoretical, if water is not added to the reaction solution. Yields of the substantially enantiomerically pure dihydrate salt of about 70 to 90% are possible by the process of the present invention.

The solid crystalline enantiomeric hydrated salt of the aryl-substituted aliphatic carboxylic acid is separated from the mother liquor by any conventional method (centrifugation, filtration, decantation, etc.) The liquid remaining, the mother liquor, can then be partially evaporated or cooled or treated in any conventional manner to recover the residual carboxylic acid.

It should be noted that the order of mixing the components of this reaction system are not important to achieve the production of the substantially pure enantiomeric salt of the compounds of formula I. Thus, the inorganic base and water can be admixed with the compounds of formula I and an inert solvent. The inorganic base and inert solvent can also be mixed with water and the compounds of formula I.

It has been discovered that each of the salts formed from the reaction of inorganic base with aliphatic carboxylic acids of formula I exhibits a unique solubility phase diagram, i.e. a plot of the solubility versus enantiomeric composition.

The eutectic point in such phase diagrams represents the most soluble composition of the mixture of enantiomers. If a solid enriched mixture of enantiomers is admixed with a solvent either all or part of the mixture will dissolve. If a sufficient amount of solvent is added so that the entire mixture becomes a solution, then cooling the solution (or evaporating some of the solvent or adding a nonsolvent, or any other conventional method used to precipitate solutes from solutions) will precipitate a portion of the salt. Depending on where the eutectic point lies the precipitated salt may be more highly enriched in one of the enantiomers or it may approach the composition of the racemic mixture. If the latter case occurs, obviously, the mother liquor will be more highly enriched than the initial aliphatic carboxylic acid enriched with one of the enantiomers.

Thus, the substantially pure salt formed from the enriched mixtures of compounds of formula I must have the following properties:
  i) at least one eutectic point;
  ii) a composition that is not at the eutectic point; and
  iii) a eutectic composition that is closer to the racemic composition than is the composition of the mixture represented by the compounds of formula I.

In the phase diagram then, if the eutectic point is at the racemic composition, an enantiomeric mixture of 70% d(+) [and 30% l(−)] upon cooling preferentially forms the most soluble fraction of 50% d(+) and 50% l(−) [the racemic composition]. The precipitated product will then have a higher concentration of S(+) than the starting composition.

Conversely, where the starting enantiomeric enriched mixture is 30% d(+) [and 70% l−)], the precipitated product will have a higher concentration of the l(−) enantiomer. It is less soluble than the racemic mixture which preferentially forms. It should be understood, however, that the composition represented by the eutectic point should not act as a solvent (does not further dissolve) the precipitated salt.

The crystalline residue isolated in the above step is substantially pure enantiomeric material. However, it should be understood that the actual purity of such "substantially pure enantiomer" is dependent on the composition of the starting enantiomerically enriched carboxylic acid. Thus, by carrying out the process of this invention using a carboxylic acid of Formula I having an optical purity of 88% d(+)-enantiomer, the process of this invention yields the substantially pure enantiomeric salt, i.e., an 99% d(+) pure product. Compositions of greater enrichment in, for example, the d(+) isomer yield final product of even higher purity, i.e., an 90% d(+) composition produces the substantially pure enantiomeric salt as a greater than 99% d(+) pure product. The process of this invention provides, in one step, a product that is obtained by the prior art processes mentioned earlier in numerous steps. As such, the process provides a more simplified method of obtaining highly pure enantiomeric salts in improved yields of the carboxylic acids than previously available.

The purified salt obtained from the process of the present invention may be further treated to produce the free aliphatic carboxylic acid thereof by using any conventional means. For example, hydrolysis of the salt with a dilute mineral acid and extraction with a suitable organic solvent produces the purified aliphatic carboxylic acid. Further extraction and recrystallization with a suitable solvent can increase the purity to even a greater extent.

The following examples are for illustration only and are not intended as limiting the invention in any way.

EXAMPLES

EXAMPLE 1

To a solution of 100 g (0.48 mol) ibuprofen [optical purity=92% d(+)] in 350 g hexane was added 9.7 g NaOH (0.24 mol). The reaction mixture was heated to 65° C., and the water of neutralization was removed by azeotropic distillation over 2.75 hours. Once the theoretical amount of water was removed, the reaction mixture was cooled to 5° C. over 2 hours and held at 5° C. for 0.25 hour. No precipitate formed, therefore the solution was seeded with 0.05 g of the sodium salt of d-(+)-Ibuprofen and the contents agitated at 5° C. for 16 hours; again no precipitate formed. To induce precipitation, 4.0 g water (0.24 mol) was added, and the dihydrate form of the sodium salt precipitated from solution within 10 min (31.3 g 48.9% based on NaOH) with an optical purity of 97.0% d(+). The identity of the dihydrate was determined by Karl-Fisher analysis, which indicated that the solid contained 13.7% water (theory for the dihydrate form is 13.63%).

EXAMPLE 2

To a solution of 120 g (0.58 mol) of ibuprofen [90% d(+)] in 420 g hexane was added 11.5 g NaOH (0.29 mol). The contents were heated to 65° C. to promote deprotonation and dissolution of the sodium salt, then cooled to 22° C. over 2 hours. The mixture was maintained at 22° C. for 1 hour, and the solid product (22.5 g, 37.5% based on NaOH, 18.8% based on added ibuprofen) was isolated by vacuum filtration. The isolated product had an optical purity of 99.3% d(+).

EXAMPLE 3

A mixture of 100.4 g ibuprofen (90 d(+)—), 350 g hexane and 9.8 g sodium hydroxide was stirred at room temperature for 3 days. The mixture then cooled to 5° C. and the resulting solids were collected by filtration. The mother liquor was combined with 4.4 g water, cooled at 5° C. and the resulting solids were isolated and combined with the first crop. The combined salt was washed with hexane and air dried. The yield was 40.1 g (63.5%) and the optical purity was 98.5 wt % d(+).

EXAMPLE 4

To a solution of 100 g (0.48 mol) ibuprofen [90% d(+)] in 350 g hexane was added 9.7 g NaOH (0.24 mol). The contents were heated to 55° C. to effect dissolution. Once the contents were in solution, 4.0 g (0.24 mol) water was added, and the contents cooled to 5° C. isolation by vacuum filtration followed by washing with 2×100 g of hexane, gave 43.1 g product (67.3% based on NaOH, 37.7% based on ibuprofen) with an optical purity of 99.7% d(+).

EXAMPLE 5

A mixture of 100.3 g ibuprofen (90 wt % d(+)enantiomer), 682 mL hexane, 10 g sodium hydroxide, and 9.7 g water was stirred and heated at reflux for 2 hours. The mixture was allowed to cool while an additional 682 mL hexane was added. The mixture was cooled to 5° C. and the resulting salt was isolated by filtration, washed with hexane and air dried. The yield of the salt was 68% and the optical purity was 99.7 wt % d(+)enantiomer.

EXAMPLE 6

A mixture of 100.3 g ibuprofen (90 wt % d(+)enantiomer), 682 mL hexane, 9.9 g sodium hydroxide, and 4.2 g water was stirred and heated at reflux for 2 hours. The mixture was allowed to cool while an additional 682 mL hexane was added. The mixture was cooled to 5° C. and the resulting salt was isolated by filtration, washed with hexane and air dried. The yield of the salt was 51.4 g (78.6%) and the optical purity was 99.6 wt % d(+)enantiomer.

EXAMPLE 7

A mixture of 99.9 g ibuprofen (88 wt % d(+)enantiomer), 380 mL hexane, 12.1 g sodium hydroxide, and 8 mL water was stirred and heated at reflux for 2 hours. The mixture was cooled to 5° C. and the resulting salt was isolated by filtration, washed with hexane and air dried. The yield of the salt was 49.6 g (38.8%) and the optical purity was 97.6 wt % d(+)enantiomer.

EXAMPLE 8

A mixture of 33 g ibuprofen (90 wt % S enantiomer), 288 mL hexane and 5.4 mL 30 wt % aqueous ammonia was heated to 45° C. and then cooled to 5° C. An additional 228 mL hexane and 1 mL ammonia solution were added. The resulting salt was isolated by filtration, washed with hexane and air dried. The optical purity of the salt was 97.6 wt % d(+)enantiomer.

EXAMPLE 9

To a solution of 100.2 g (0.48 mol) ibuprofen [89.5 d(+)] in 150 g hexane Was added 11.6 g NaOH (0.29 mol) and 10.4 g water (0.58 mol). The contents were heated to 56° C. and held for 1 hour. The reaction mixture was then cooled to 5° C. over 2 hours, and the product was isolated by vacuum filtration followed by washing the cake with 2×100 g of hexane. The isolated S-(+)-ibuprofen, sodium salt dihydrate (45.7 g, 61.0% on NaOH, 36.6% based on ibuprofen), had an optical purity of 99.1% d(+).

We claim:

1. A process for producing a substantially pure enantiomeric salt of an aryl-substituted aliphatic carboxylic acid having the formula:

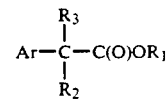

where R$_1$ is hydrogen alkyl; R$_2$ and R$_3$ different and are hydrogen, alkyl, cycloalkyl, phenyl, naphthyl, substituted phenyl, substituted naphthyl, haloalkyl, hydroxyalkyl, alkoxyalkyl, acyloxyalkyl, carboxyalkyl, alkoxycarbonylalkyl or cyanoalkyl and Ar is phenyl, naphthyl, substituted phenyl or substituted naphthyl; which comprises:
i) reacting in an inert solvent the aryl-substituted aliphatic carboxylic acid enriched with one of its enantiomers with an inorganic base and a separation-enhancing amount of water thereby forming a hydrated salt of said aryl-substituted aliphatic carboxylic acid enriched with one of its enantiomers, said water sufficient to enhance the separation of said hydrated salt, said hydrated salt having the following properties: a) at least one eutectic point; b) a composition that is not at the eutectic point; and c) a eutectic composition that is closer to the racemic composition of said hydrated salt than is the composition of said aryl-substituted carboxylic acid enriched with one of its enantiomers,
ii) separating the hydrated salt of the substantially pure enantiomer of the aryl-substituted aliphatic carboxylic acid.

2. The process according to claim 1 wherein said inorganic base is an ammonium hydroxide or a metal hydroxide, carbonate, bicarbonate or chloride.

3. The process according to claim 2 wherein the metal is from Group IA or IIA of the Periodic Table of Elements.

4. The process according to claim 3 wherein said inorganic base is sodium hydroxide.

5. The process according to claim 1 wherein the solvent is an inert organic inert solvent.

6. The process according to claim 1 wherein the ratio of said base is from about 0.05 to about 0.95 mole per mole of aryl-substituted aliphatic carboxylic acid.

7. The process according to claim 6 wherein the ratio is from about 0.45 to about 0.65 mole per mole of aryl-substituted aliphatic carboxylic acid.

8. The process according to claim 1 wherein said aryl-substituted aliphatic carboxylic acid is treated with said base at a temperature of from about 0° C. to about 125° C.

9. The process according to claim 8 where the temperature is 40° C. to 60° C.

10. The process of claim 1 wherein said aryl-substituted aliphatic carboxylic acid is 2-(4-isobutylphenyl)propionic acid.

11. The process according to claim 1 wherein the mole ratio of said separation enhancing amount of water to the aryl substituted aliphatic carboxylic acid is from 0.1 to 5.0.

12. The process according to claim 1 wherein the hydrated salt is the sodium salt of the substituted aliphatic carboxylic acid.

13. The process according to claim 12 wherein the hydrated salt is the dihydrated sodium salt of aryl-substituted carboxylic acid.

14. A process for producing a substantially pure enantiomeric salt of an aryl-substituted aliphatic carboxylic acid having the formula:

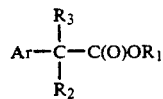

where $R_1$ is hydrogen or alkyl; $R_2$ and $R_3$ are different and are hydrogen, alkyl, cycloalkyl, phenyl, naphthyl, substituted phenyl, substituted naphthyl, haloalkyl, hydroxyalkyl, alkoxyalkyl, acyloxyalkyl, carboxyalkyl, alkoxycarbonylalkyl or cyanoalkyl and Ar is phenyl, naphthyl, substituted phenyl or substituted naphthyl; which comprises:
i) reacting in an inert solvent the aryl-substituted aliphatic carboxylic acid enriched with one of its enantiomers with an inorganic base and a separation-enhancing amount of water thereby forming a hydrated salt of said aryl-substituted aliphatic carboxylic acid enriched with one of its enantiomers, said water sufficient to enhance the separation of said hydrated salt, said hydrated salt having the following properties: a) at least one eutectic point; b) a composition that is not at the eutectic point; and c) a eutectic composition that is closer to the racemic composition of said hydrated salt than is the composition of said aryl-substituted carboxylic acid enriched with one of its enantiomers;
ii) separating the hydrated salt of the substantially pure enantiomer of the aryl-substituted aliphatic carboxylic acid; and
iii) treating said hydrated salt of the substantially pure enantiomer of the aryl-substituted aliphatic carboxylic acid to produce the substantially pure enantiomer of said aryl-substituted aliphatic carboxylic acid.

15. A process for producing a substantially pure enantiomeric of an aryl-substituted aliphatic carboxylic acid having the formula:

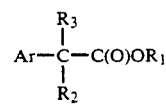

where $R_1$ is hydrogen or alkyl; $R_2$ and $R_3$ different and are hydrogen, alkyl, cycloalkyl, phenyl, naphthyl, substituted phenyl, substituted naphthyl, haloalkyl, hydroxyalkyl, alkoxyalkyl, acyloxyalkyl, carboxyalkyl, alkoxycarbonylalkyl or cyanoalkyl and Ar is phenyl, naphthyl, substituted phenyl or substituted naphthyl; which comprises:
i) reacting in an inert solvent the aryl-substituted aliphatic carboxylic acid enriched with one of its enantiomers with sodium hydroxide and a separation-enhancing amount of water thereby forming a hydrated sodium salt of said aryl-substituted aliphatic carboxylic acid enriched with one of its enantiomers, said water sufficient to enhance the separation of said hydrated sodium salt, said hydrated sodium salt having the following properties: a) at least one eutectic point; b) a composition that is not at the eutectic point; and c) a eutectic composition that is closer to the racemic composition of said hydrated sodium salt than is the composition of said aryl-substituted carboxylic acid enriched with one of the enantiomers;
ii) separating the hydrated sodium salt of the substantially pure enantiomer of the aryl-substituted aliphatic carboxylic acid; and
iii) treating said hydrated sodium salt of the substantially pure enantiomer of the aryl-substituted aliphatic carboxylic acid to produce the substantially pure enantiomer of said aryl-substituted aliphatic carboxylic acid.

16. The hydrated salt of a substantially pure enantiomeric salt of an aryl-substituted aliphatic carboxylic acid of the formula:

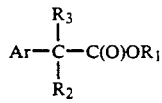

where $R_1$ is hydrogen or alkyl; $R_2$ and $R_3$ different and are hydrogen, alkyl, cycloalkyl, phenyl, naphthyl, substituted phenyl, substituted naphthyl, haloalkyl, hydroxyalkyl, alkoxyalkyl, acyloxyalkyl, carboxyalkyl, alkoxycarbonylalkyl or cyanoalkyl and Ar is phenyl, naphthyl, substituted phenyl or substituted naphthyl; the water of hydration of said hydrated salt being produced as the product of the reaction of an inorganic base and said aryl-substituted aliphatic carboxylic acid the hydrated salt produced from the process comprising:

i) reacting in an inert solvent an aryl-substituted aliphatic carboxylic acid enriched with one of its enantiomers with an inorganic base and a separation-enhancing amount of water thereby forming said hydrated salt of said aryl-substituted aliphatic carboxylic acid enriched with one of its enantiomers, said water sufficient to enhance the separation of said hydrated salt, said hydrated salt having the following properties: a) at least one eutectic point; b) a composition that is not at the eutectic point; and c) a eutectic composition that is closer to the racemic composition of said hydrated salt than is the composition of said aryl-substituted carboxylic acid enriched with one of its enantiomers;

ii) separating the hydrated salt of the substantially pure enantiomer of the aryl-substituted aliphatic carboxylic acid.

17. The salt according to claim 16 wherein Ar is substituted phenyl and $R_2$ is alkyl and $R_3$ hydrogen.

18. The salt according to claim 17 wherein Ar is p-isobutylphenyl and $R_2$ is methyl.

19. The salt according to claim 18 that is the dihydrate.